US006346102B1

(12) United States Patent
Harrington et al.

(10) Patent No.: US 6,346,102 B1
(45) Date of Patent: *Feb. 12, 2002

(54) METHOD AND APPARATUS FOR TUBAL OCCLUSION

(75) Inventors: Douglas C. Harrington; Brett Bowman; Peter M. Breining, all of Santa Clara, CA (US)

(73) Assignee: Adiana, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/579,976

(22) Filed: May 26, 2000

Related U.S. Application Data (63) Continuation of application No. 09/372,394, filed on Aug. 10, 1999, now Pat. No. 6,068,626, which is a continuation of application No. 09/063,119, filed on Apr. 20, 1998, now Pat. No. 5,954,715.
(60) Provisional application No. 60/048,632, filed on Jun. 5, 1997, and provisional application No. 60/054,388, filed on Jul. 31, 1997.

(51) Int. Cl.⁷ ............................................... A61B 17/38
(52) U.S. Cl. ......................................... 606/28; 128/831
(58) Field of Search .............................. 606/28, 48, 27, 606/42, 43, 135; 128/831, 898

(56) References Cited

U.S. PATENT DOCUMENTS

| 2,102,270 A | 12/1937 | Hyams ................... 128/303.17 |
| 3,680,542 A | 8/1972 | Cimber ....................... 128/1 R |
| 3,805,767 A | 4/1974 | Erb ............................. 128/1 R |
| 3,840,016 A | 10/1974 | Lindemann ............. 128/303.17 |
| 3,858,571 A | 1/1975 | Rudolph ..................... 128/1 R |
| 3,858,586 A | 1/1975 | Lessen .................... 128/303.1 |
| 3,918,431 A | 11/1975 | Sinnreich .................... 128/1 R |
| 3,938,527 A | 2/1976 | Rioux et al. ........... 128/303.17 |
| 3,953,566 A | 4/1976 | Gore .......................... 264/288 |
| RE29,345 E | 8/1977 | Erb ............................. 128/1 R |
| 4,057,063 A | 11/1977 | Gieles et al. ........... 128/303.17 |
| 4,474,179 A | 10/1984 | Koch ...................... 128/303.17 |
| 4,606,336 A | 8/1986 | Zeluff ......................... 128/130 |
| 4,700,701 A | 10/1987 | Montaldi ............... 128/303.17 |
| 4,834,091 A | 5/1989 | Ott ........................... 128/303.1 |
| 4,966,597 A | 10/1990 | Cosman ....................... 606/50 |
| 5,009,655 A | 4/1991 | Daignault, Jr. et al. ......... 606/7 |
| 5,095,917 A | 3/1992 | Vancaillie .................... 128/831 |
| 5,122,137 A | 6/1992 | Lennox ........................ 606/40 |
| 5,147,353 A | 9/1992 | Everett ........................ 606/15 |
| 5,152,784 A | 10/1992 | Tsilibary ....................... 623/1 |
| 5,167,658 A | 12/1992 | Ensslin ........................ 606/34 |

(List continued on next page.)

FOREIGN PATENT DOCUMENTS

| WO | WO 96/40023 | 12/1996 |
| WO | WO 96/40024 | 12/1996 |

OTHER PUBLICATIONS

Neuwirth, Update On Transcervical Sterlization, 51 International Journal of Gynecology & Obstetrics, Suppl. 1, S23–28 (1995).
Quinones Guerror, Tubal Electrocauterization Under Hysteroscopic Control, 7 Contraception 195–201 (Mar. 1973).
Quinones, Hysteroscopic Sterilization, 14 International Journal of Gynecolgoy & Obstetrics 27–34 (1976).

(List continued on next page.)

Primary Examiner—Kevin Truong
(74) Attorney, Agent, or Firm—K. David Crockett, Esq.; Crockett & Crockett (57) ABSTRACT

A device for sterilizing females by occluding the uterotubal junction. The device includes a catheter with a releasable heat generating plug which is used to thermally damage the uterotubal junction and cause it to constrict around the plug, after which the plug is released from the catheter and left in place in the uterotubal junction.

4 Claims, 9 Drawing Sheets

U.S. PATENT DOCUMENTS

| | | | | |
|---|---|---|---|---|
| 5,303,719 A | 4/1994 | Wilk et al. | | 128/898 |
| 5,383,922 A | 1/1995 | Zipes et al. | | 607/122 |
| 5,536,267 A | 7/1996 | Edwards et al. | | 606/41 |
| 5,556,396 A | 9/1996 | Cohen et al. | | 606/42 |
| 5,569,245 A | 10/1996 | Guglielmi et al. | | 606/49 |
| 5,569,462 A | 10/1996 | Martinson et al. | | 424/424 |
| 5,589,176 A | 12/1996 | Seare, Jr. | | 424/400 |
| 5,601,600 A | 2/1997 | Ton | | 606/206 |
| 5,605,693 A | 2/1997 | Seare, Jr. | | 424/400 |
| 5,632,767 A | 5/1997 | Sinofsky | | 607/89 |
| 5,635,482 A | 6/1997 | Bhatnagar | | 514/14 |
| 5,643,253 A | 7/1997 | Baxter et al. | | 606/17 |
| 5,643,257 A | 7/1997 | Cohen et al. | | 606/48 |
| 5,649,924 A | 7/1997 | Everett et al. | | 606/15 |
| 5,658,282 A | 8/1997 | Daw et al. | | 606/49 |
| 5,743,905 A | 4/1998 | Eder et al. | | 606/32 |
| 5,785,705 A | 7/1998 | Baker | | 606/32 |
| 5,800,529 A | 9/1998 | Brauker et al. | | 623/11 |
| 5,827,269 A | * 10/1998 | Saadat | | 606/28 |
| 5,891,457 A | * 4/1999 | Neuwirth et al. | | 128/831 |

OTHER PUBLICATIONS

Brumsted, Attempted Transcervical Occulsion of the Fallopian Tube With The ND: Yag Laser, 77 Obstetrics and Gynecolgy 327–28 (Feb. 1991).

Thompson, Vessel Occlusion With Trancatheter Electrocoagulation: Initial Clinical Experience, 133 Radiology 335–340 ( Nov. 1979).

Phillips, Experimental Closure Of Arteriovenous Fistula By Transcatheter Electrocoagulation, 115 Radiology 319–21 (May 1975).

Coleman, The Foreign Body Reaction: A Chronic Inflammatory Response, 8 J. Biomed. Mater. Res. 199–211 (1974).

Pollack, Wound Healing; A Review, 5:5 J. Dermatol. Surg. Oncol. 389 (May 1979).

Tibbs, Wound Healing Following Radiation Therapy; A Review, 42 Radiology and Oncology 99–106 (1997).

Sahwi, The Leukocytic Response to an Intrauterine Foreign Body in the Rabbit, 22 Fertiltiy and Sterility 398 (Jun. 1971).

Kearney, Patent Cooperation Treaty Written Opinion, International Application No. PCT/US98/08111, Date of Mailing Feb. 22, 1999.

* cited by examiner

METHOD AND APPARATUS FOR TUBAL OCCLUSION

This application is a continuation of U.S. application Ser. No, 09/372,394 filed Aug. 10, 1999 now U.S. Pat. No. 6,068,626, which is a continuation of U.S. application Ser. No. 09/063,119 filed Apr. 20, 1998 now U.S. Pat. No. 5,954,715, which is a continuation-in-part of U.S. provisional patent applications 60/048,632 filed Jun. 5, 1997 and 60/054,388 filed Jul. 31, 1997.

FIELD OF THE INVENTION

The present invention relates to an apparatus and method for permanently closing body vessels such as veins, arteries, body tubes, etc. The present invention particularly, though not exclusively, relates to the occlusion of the female mammalian fallopian tubes. In particular, this invention is directed to a relatively simple surgical procedure for sterilizing human females which may be performed in the physician's office.

BACKGROUND OF THE INVENTION

It is often desired or necessary for medical reasons to permanently close body vessels such as veins, arteries, body tubes, etc. Of particular utility is an ability to close the fallopian tubes of women for sterilization purposes.

One method for sterilization in females is surgical tubal ligation, a procedure in which the uterine tubules are tied and cut or clamped through an incision made through the wall of the abdomen. When done endoscopically, the pelvic cavity must be pneumatically inflated using an inert gas. Aside from injury due to over inflation, numerous cases of the formation of embolisms have been reported. Tubal ligation done with a laparotomy requires a surgical incision in the abdomen between 6 and 12 centimeters long done under general anesthesia. Aside from permanent scar formation at the site of incision, there are reported cases of death due to anesthesia complications.

Other methods for female sterilization have been investigated. In one technique, investigators have transcervically instilled the sclerosing agent quinacrine into the uterus and fallopian tubes to create a permanent closure of the fallopian tubes. Major drawbacks from this procedure are the need of repeat applications and a significant level of side effects.

Another technique involves transcervically injecting a curable elastomeric composition such as silicone into the fallopian tubes in an amount sufficient to fill the portion of the oviduct adjacent the uterus. The elastomeric composition is allowed to solidify to thereby nonsurgically block the tube. Erb, *Method and Apparatus for No-Surgical, Reversible Sterilization of Females*, U.S. Pat. No. 3,805,767 (Apr. 23, 1974). This technique is time consuming, however, and requires a high level of technical skill both for the preparation of the silicone and for performing the procedure.

Cohen, et al, *Method for Tubal Electroligation*, U.S. Pat. No. 5,556,396 (Sep. 17, 1996) discloses a method for tubal ligation by providing an electrically energizable electrode to a fallopian tube. The electrode is advanced into the fallopian tube and energized to thermally damage the fallopian tube, thereby causing enough scarring of the fallopian tube to permanently occlude it. The Cohen patent is hereby incorporated by reference.

Others have proposed placement of an occlusive wire or coil within the fallopian tubes to occlude them. Ton, Endoluminal Coil Delivery System having a mechanical release mechanism, U.S. Pat. No. 5,601,600 (Feb. 11, 1997), proposes placement of a Guglielmi detachable coil (typically used for vascular occlusion) deep within the fallopian tube, past the isthmus. The coil must be delivered into the fallopian tubes with a delivery catheter extending from the uterus into the fallopian tubes.

Many of the prior art sterilization methods require placement of an occluding object or device deep within the fallopian tube. Theoretically, the prior art devices make sense. However, the fallopian tubes have proven to be very difficult to cross with any useful device. In the typical human anatomy, catheters and guidewires cannot always navigate through the fallopian tubes as required by the methods of the prior art.

SUMMARY

The method of the present invention provides a technique of sterilization, discussed in greater detail below, which involves the collapsing of the uterotubal junction and/or fallopian tube around a plug to create total occlusion of the tube. Total occlusion of the tube prevents male sperm from fertilizing female eggs, thus preventing conception.

The method comprises, in accordance with the present invention, the steps of: (a) providing an elongated instrument assembly having a distal end portion, (b) inserting the distal end portion of the instrument assembly through the vagina, across the cervix, and into the patient's uterotubal junction (uterotubal junction), (c) operating the instrument assembly to deliver and control radio frequency (RF) energy from the instrument, causing the tissue of the uterotubal junction to collapse on the distal end portion, (d) detaching the distal portion of the instrument to create a total seal of the uterotubal junction, (e) removing the remaining portion of the instrument from the patient.

The method can be modified to permit the sterilization of both fallopian tubes without removal and replacement of the catheter from the uterus to sterilize the second tube.

The fact that the tissue destruction is performed outside the fallopian tubes, close to the uterine cavity in the thick portion of the uterotubal junction substantially reduces the risk of bowel injury. Advancement of any device beyond the isthmus of the fallopian tubes or within the fallopian tubes is not necessary, although in some cases insertion into the proximal portion of the fallopian tubes will be accomplished. No caustic substances come into contact with the peritoneum, obviating unpleasant side effects, and total occlusion of the lumen virtually eliminates the risk of ectopic pregnancy. Furthermore, no special technique is required to perform the procedure.

DETAILED DESCRIPTION OF THE INVENTION

Figure 1:
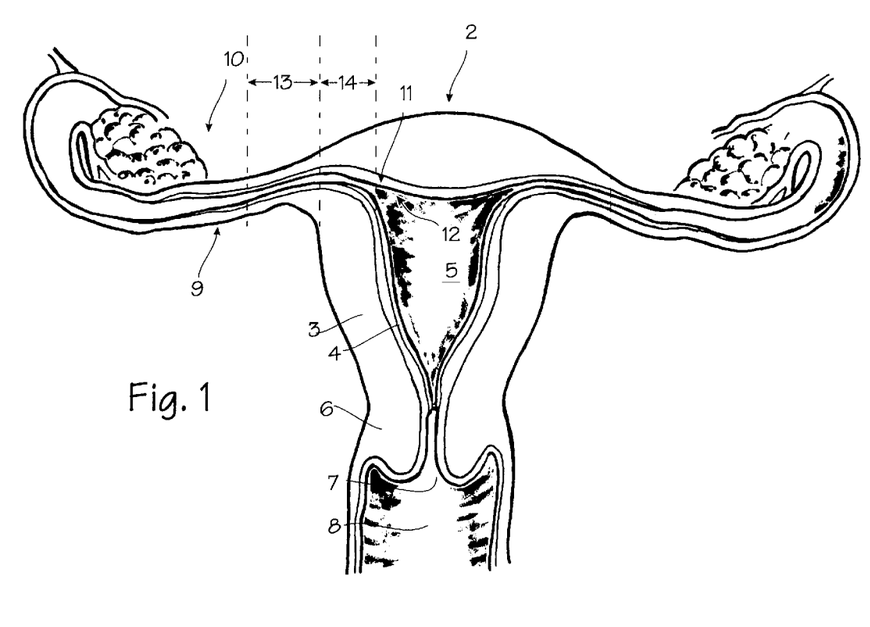
FIG. 1 is a partial view of the female reproductive system.

FIG. 1 shows some of the major elements of the female reproductive system. The uterus 2 is an organ of the female pelvis that has the shape of a pear. It consists of a thick muscular coat, the myometrium 3, a cavity having an inner mucosal lining of variable thickness called the endometrium 4, and a cavity referred to as the uterine cavity 5. The cervix 6 defines the cervical canal 7 which is an inferior opening to the vagina 8. The fallopian tube 9 is a hollow organ that connects the uterus to the ovary 10. The ovary is the organ that produces one or more eggs during every cycle of a woman's reproductive life. In the human female reproductive system, there is one uterus, two fallopian tubes and two ovaries (under normal conditions). The site where the fallopian tube and uterus connect is called the uterotubal junction 11. It is a section of tubular shape of about 10 mm in length. Its inner diameter in the resting position is less than 1 mm, but when gas or liquid is pushed through the uterus and tubes, the diameter of the uterotubal junction may stretch up to about 2 mm. The uterotubal junction provides a transition between the uterus and the fallopian tube, and the area of transition from the chamber of the uterus to the lumen of the uterotubal junction is referred to as the ostium or cornu (marked with item number 12). The area of transition between the ostium and the isthmus 13 of the fallopian tube is referred to as the interstitial portion (marked as item 14). The ostium, uterotubal junction, interstitial portion, isthmus and fallopian tube are part of a pathway leading from the ovaries to the uterus, and this pathway is sometimes referred to as the uterine tube.

Figures 2, 2A, 2B:
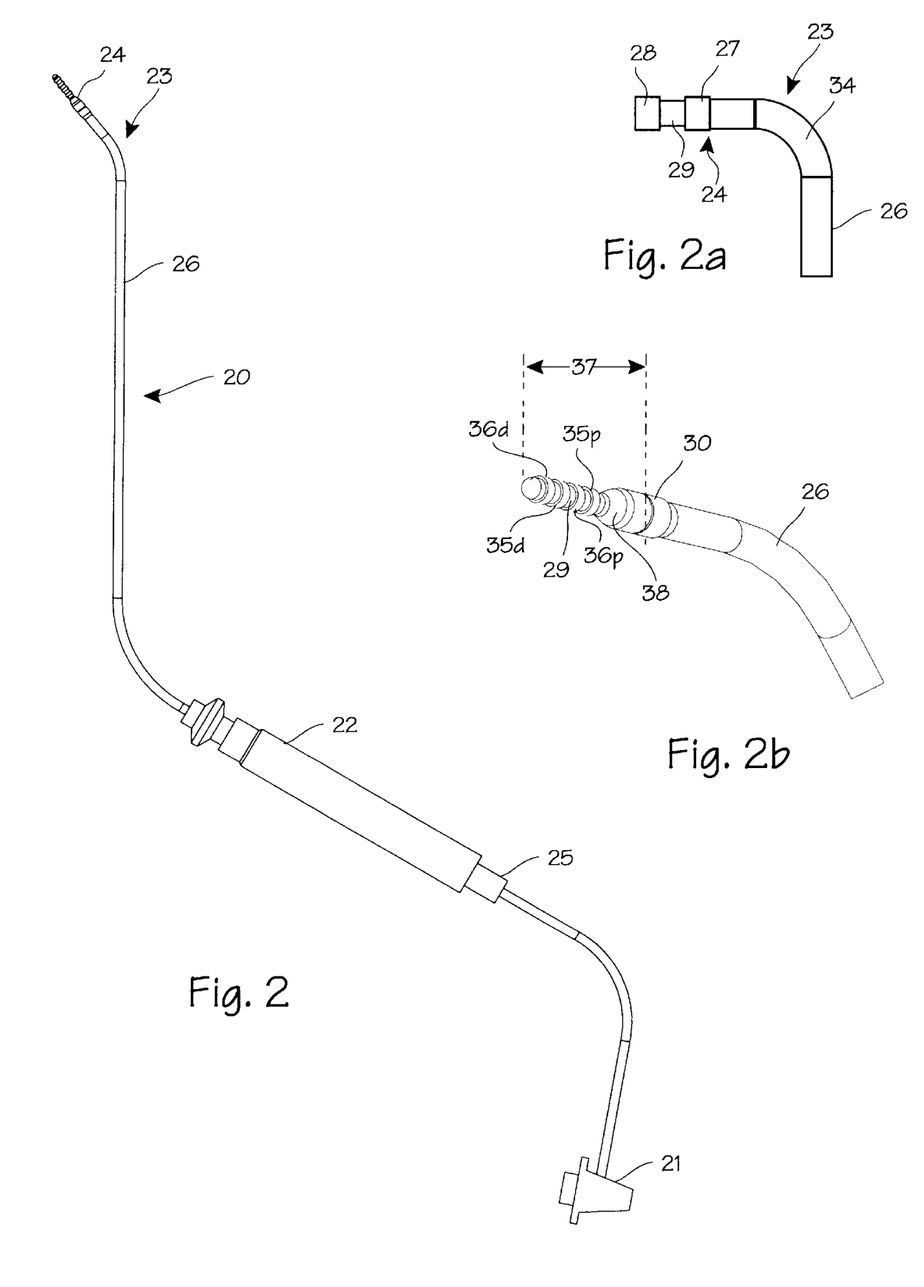
FIG. 2 is a drawing of the device used to deliver RF power and an occluding plug to the uterotubal junction.
FIGS. 2a and 2b are close up views of the distal segment of the device including bipolar electrodes.

FIG. 2 shows the main components of the present invention. The first is an elongated tubular segment, better known as a catheter 20, that contains several significant components. The proximal section of the catheter contains an electrical connector 21 to connect to an RF generator. Also located at the proximal section of the catheter is a deflection handle 22. When the handle is manipulated, the distal section 23 of the catheter bends in a relative direction by means of a manipulation wire connected between the handle and distal catheter section. By operating the actuator means on the handle, the distal tip bends 30 to 180 degrees from straight. (Where the transcervical catheter is used in conjunction with a steerable hysteroscope, the catheter itself need not be steerable.) The detachable electrode plug 24 is mounted on the catheter at the distal end of the catheter, and the proximal actuator 25 is mounted on the handle and connected to a detachment mechanism within the distal tip of the catheter.

The middle section of the catheter 26, (body), consists of a hollow tubular structure that contains the conductor(s), sensor wires, manipulation device and distal section anchor/ release mechanism. This section protects the human body from these components and is required to deliver the distal tip portion to the proper location. The middle section can be manufactured with stainless steel wire braid or winding to improve torque transfer. Improved torque transfer helps assist the doctor with twisting the handle on the proximal end of the device allowing for the torque to transfer to the distal section of the device and aid in proper placement of the distal section to the uterotubal junction. A coating can be applied to the shaft to increase its radiopacity for X-ray procedures. The coating may include compounds such as a barium sulfate loaded urethane or Pebax™ manufactured by Atochem. In addition, an echogenic coating can be applied to the shaft to increase the catheter's visibility during ultrasound imaging. This coating can include trapped air bubbles that provide an echogenic effect. The catheter shaft may be made with a material loaded with air bubbles as well. Catheter shaft materials can be, but are not limited to PTFE sold under the tradename of Teflon® manufactured by DuPont, ETFE, polyethylene, polypropylene and polyvinylchloride.

FIG. 2a shows a simple bipolar embodiment for the detachable electrodes on the distal section 23 of the catheter. The electrode plug 24 contains the proximal electrode 27, distal electrode 28, and the insulator 29 to electrically and thermally insulate the electrodes, the anchor/release mechanism 30 for the electrode and a temperature sensor. It also contains a soft catheter portion 34 to allow deflection when the proximal handle is manipulated. One conductor wire is attached to the distal electrode and a second conductor wire is attached to the proximal electrode. The length of the conductors is contained within the catheter body to isolate it from the patient. The conductors are coated with an electrically insulative material. The proximal end of each conductor is attached to the electrical connector 21. The electrical connector is then connected to an RF generator.

FIG. 2b illustrates another embodiment for the bipolar electroded plug 24. The electrode assembly includes two hot electrodes 35d and 35p, and two ground electrodes 36d and 36p mounted on the insertion portion 37 of the electrode plug 24. The insertion portion comprises the insulator 29 and the electrodes. The attachment mechanism 30 attaches to the soft catheter portion 34, and is housed within the proximal section of the electrode plug 24. The proximal section of the plug may be provided with a larger diameter cross section than the insertion portion, in order to form a shoulder or flange type surface 38 which will serve to limit insertion of the plug and prevent insertion into the fallopian tubes.

The distal electrodes can be made from any electrically conductive material such as stainless steel, copper, Elgiloy™, MP35N, platinum, titanium, nitinol and various other materials and alloys. The surface of the distal electrode can be covered or finished with a porous design to encourage fibroblast and/or tissue ingrowth. Tissue ingrowth (possibly referred to as scar formation) around the electrode insures a permanent seal of the fallopian tube. Different shape configurations and undercuts can also be incorporated into the electrode design to insure a permanent seal of the fallopian tube. Various embodiments of bipolar and monopolar plugs may be adapted for use. For a monopolar device, there is only one electrode on the distal section of the catheter. A dispersive electrode placed on the patient's exterior creates the current path for the monopolar device. While this is unsuitable for devices attempting thermal damage of the thin-walled fallopian tube, it should be suitable for the thick portion of the uterotubal junction. The insulator 29 can be made from any of the thermal and electrically insulative engineering materials such as ceramic, polyetheretherketone, Ultem™ manufactured by General Electric, phenolic, epoxy, Pebax™ and PTFE. The surface of the insulator can be covered or finished with a porous design to encourage fibroblast ingrowth. The insulator can be manufactured from porous expandable material such as Teflon. Use of expanded PTFE encourages tissue ingrowth and/or scar formation around the electrode insuring a permanent seal and preventing plug migration over time. The insulator may be a coating applied over a conductive material.

The insulator can also be made from any of the bioresorbable or bioerodible materials such as polyglycolic acid (PGA), polylactic acid (PLA), polydioxanone (PDS), or any combination of them. The insulator material can also be attached to the distal section of the plug to encourage tissue ingrowth and/or scar formation distally from the plug in the fallopian tube.

The proximal electrode 27 can be made from any electrically conductive material such as stainless steel, copper, Elgiloy™, MP35N, platinum, titanium, or nitinol or other alloys. The proximal electrode can be larger than the distal electrode. This creates a higher current density in the tissue adjacent to the distal electrode and insulator, so that collapse of the fallopian tube is more pronounced in the insulator and distal electrode portion.

The distal portion can also contain a temperature sensing device such as a thermocouple or thermistor. The sensor is connected for feedback to a control circuit that modulates RF power applied to the electrodes according to the signal received from the temperature sensor. The control circuit compares the signal from the temperature sensor to a set value and modulates the RF power applied to the electrode in accordance with the set value. A predetermined temperature setting can also be used to stop RF power delivery to the electrode. In this way over-heating of the uterotubal junction can be prevented and the possibility of bowel perforation minimized.

The procedure can be done under x-ray guidance, sonographically, hysteroscopically, or blindly. The procedure can be done under general and local anesthesia or general anesthesia only or local anesthesia only, with the latter preferred. The device is inserted into the body non-invasively: through the vagina, through the cervix into the uterus. This device can be inserted into another device such as a hysteroscope already positioned across the cervix.

By manipulating the proximal handle, the distal segment can be deflected to assist in proper positioning of the distal electrode within the uterotubal junction or fallopian tube ostium or fallopian tube.

Impedance measurements are taken from the tip electrode (s) to assist with proper positioning. For a bipolar device design, in the presence of an electrolyte distention media (such as saline solution), impedance will increase when the electrode is positioned properly within the uterotubal junction. It has been shown that this rise in current resistance is due in part to the current path moving from the electrically conductive media into the relatively higher resistant tissue within the uterotubal junction.

For a bipolar device in the presence of a non-electrolyte distention media (such as sorbitol), impedance will decrease when the electrode is positioned properly within the uterotubal junction. It has been shown that this decrease in current resistance is due in part to the current path moving from the non-electrically conductive media into the relatively lower resistant tissue within the uterotubal junction.

For monopolar electrodes, in the presence of a non-electrolytic distention media, the impedance will decrease when the electrode is positioned properly within the uterotubal junction. It has been shown that this decrease in current resistance is due in part to the current path moving from the non-electrically conductive media into the relatively lower resistant tissue within the uterotubal junction. Impedance monitoring can be accomplished through the electrode plug in the RF embodiments, and it can be accomplished with the addition of impedance sensing electrodes in the laser and ultrasound embodiments.

It is also possible with the current device to deliver a local anesthesia to the uterotubal junction before the delivery of RF, laser or ultrasound energy. This will prevent any discomfort to the patient during the procedure. It can be delivered in a liquid, gel, paste or pill form directly to the site. It can also be loaded into the electrode(s), laser hot tip, or ultrasound heating element, or into other parts of the device such as the insulating portions of the RF electrode assembly.

When the electrode plug is in position, controlled delivery of RF current to the electrode(s) causes constriction of the vessel around the distal electrode and insulator. Temperature and/or impedance monitoring can be used to control or terminate RF current delivery to the electrode. For temperature, the control circuit compares the signal from the temperature sensor to a set value and modulates the RF power applied to the electrode in accordance with the set value. A predetermined temperature setting can also be used to stop RF power delivery to the electrode. For impedance, the control circuit compares the signal from the electrode(s) to a set value and modulates the RF power applied to the electrode(s) in accordance with the set value. A predetermined impedance setting can also be used to stop RF power delivery to the electrode.

Figure 3:
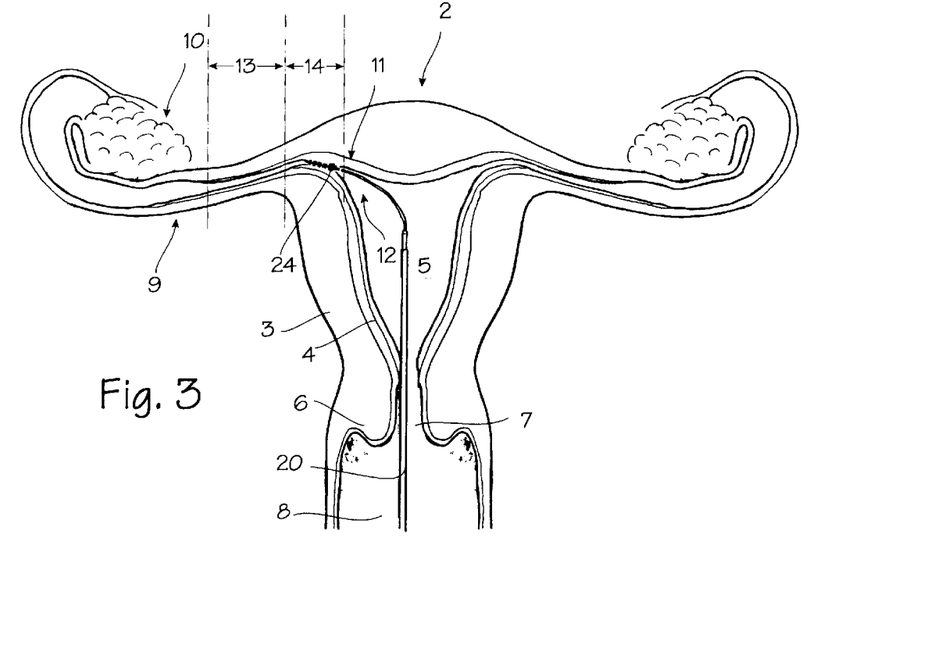
FIG. 3 is a drawing of the device with the distal section placed within the uterotubal junction before delivery of RF energy and detachment of the electrode (plug).
Figure 3A:
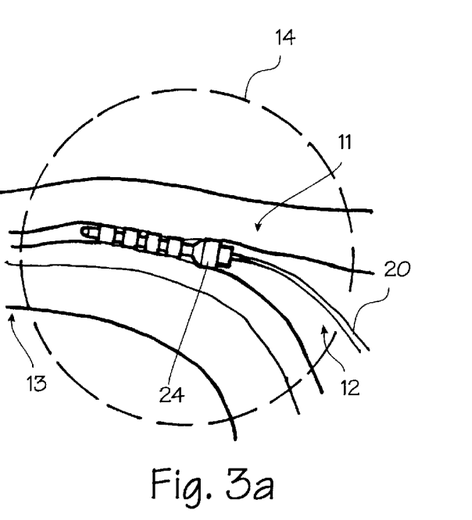
FIGS. 3a and 3b are close-up views of the uterotubal junction before and after delivery of RF energy, illustrating detachment of the distal portion and removal of the remaining portions of the device.
Figure 3B:
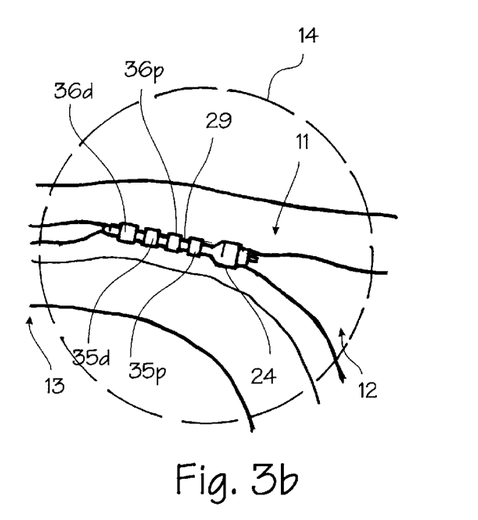

FIGS. 3 through 3b illustrate the procedure. FIG. 3 shows the uterus and the structures of FIG. 1, including the uterus 2, cervix 6, vagina 8, fallopian tubes 9, uterotubal junction 11, the interstitial portion 14 and the ostium 12. The catheter 20 has been inserted through the vagina and across the cervix to the area of the ostium. The electrode plug 24 has been advanced into the uterotubal junction 11, until the shoulder of the plug meets the junction and inhibits further insertion (the surgeon will feel increased resistance to advancement, and will be able to visually observe impact of the shoulder). Note that electrode plug 24 is inserted into a fairly thick area of the uterotubal junction 11 and the interstitial portion, and has not entered the isthmus 13 or the thin walled portion of the fallopian tube 9. Insertion only into the extra-fallopian length of the lumen will prevent the possibility of burning or puncturing a hole in the fallopian tube and surrounding structures. FIG. 3a shows the electrode plug 24 mounted on the catheter distal tip 23 and inserted into the uterotubal junction 11 before heating of the plug and surrounding tissue with RF energy. The surrounding tissue of the uterotubal junction has been thermally injured and has swollen around the plug and into the gaps between the electrodes. When sufficient occlusion has been accomplished, the distal electrode and insulator are detached from the body of the catheter. This is accomplished by operating the proximal actuator illustrated in FIG. 2. FIG. 3b illustrates the plug after separation of the plug from the remainder of the device. The electrode plug 24, including the electrodes 36d, 36p, 35d, and 35p, and the insulator 29, remain within the uterotubal junction. The surrounding tissue will heal in this condition, essentially surrounding and encapsulating the electrode plug to create a mechanical lock on the plug. The electrode plug may be made in other embodiments which permit detachment of the distal electrode section from the remainder of the plug. In this case, a distal electrode and insulator remain in place while the remaining portion of the catheter, including the proximal electrodes, are removed from the body. In yet another embodiment of the invention, there are several electrodes attached to the distal catheter to allow the physician to occlude both fallopian tubes without withdrawal of the device. The electrode(s) and insulator are designed to encourage fibroblast ingrowth to create a hermetic seal and prevent electrode migration.

Figure 4A:
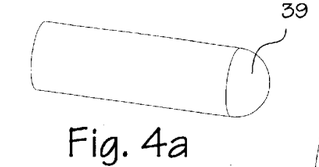
FIGS. 4–7 describe various electrode designs for use with the device.
Figure 4B:
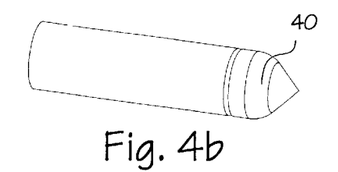
Figure 4C:
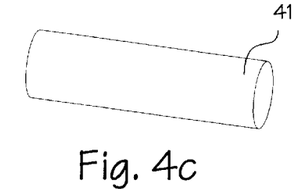
Figure 4D:
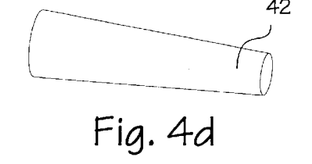
Figure 5A:
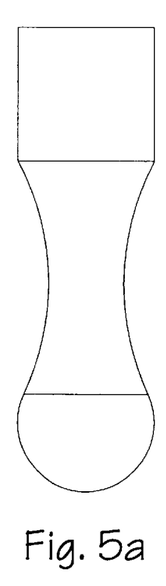
Figure 5B:
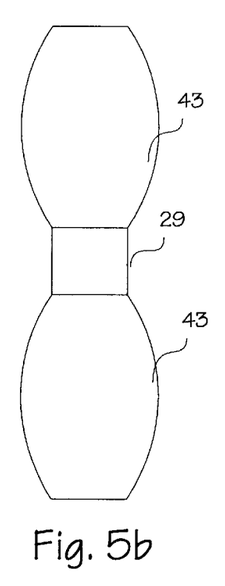
Figure 5C:
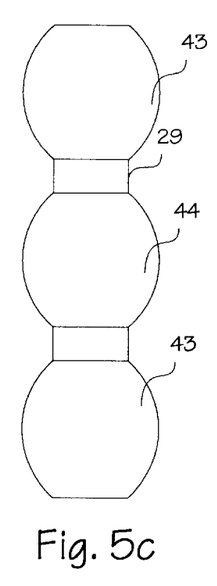
Figure 5D:
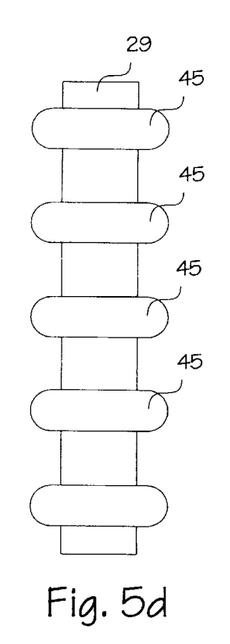
Figure 6A:
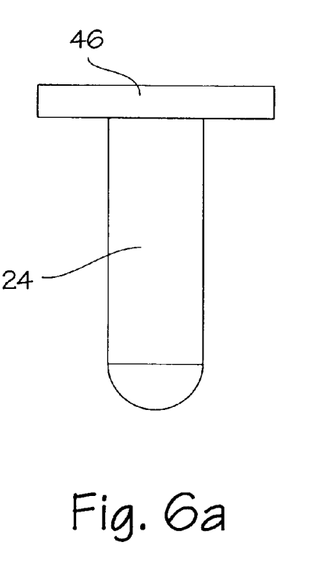
Figure 6B:
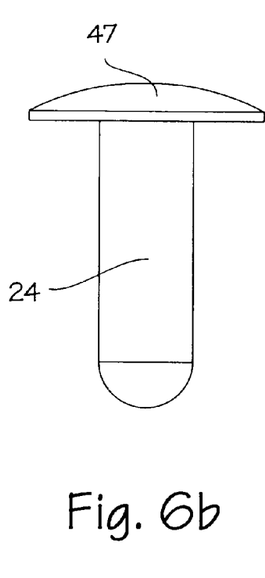
Figure 6C:
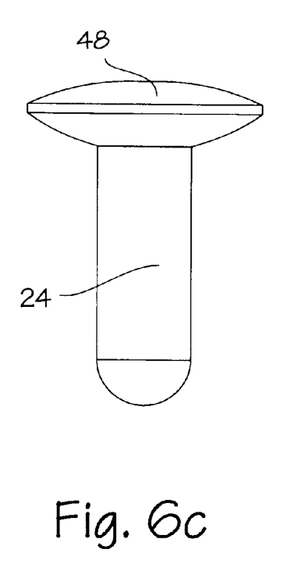
Figure 7:
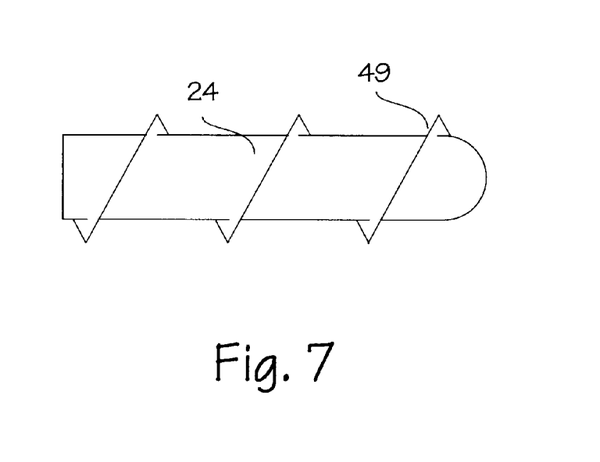

FIGS. 4a through 4d illustrate various shapes for electrodes in the simplest embodiment of the device. FIG. 4a is a cylindrical plug with a ball point 39 at the distal end of the plug. FIG. 4b is a cylindrical plug with a bullet point 40 at the distal end of the plug. FIG. 4c is a cylindrical plug with a flat cylinder top 41 at the distal end of the plug. FIG. 4d is a frustoconical plug with the small end 42 at the proximal end of the plug (it can be reversed). FIGS. 5a–5c illustrate embodiments of the electrode plug which provide for mechanical interlocking relationship between the shrunken uterotubal junction and the electrode. FIG. 5a shows a pawn shaped electrode. FIG. 5b shows a barbell shaped electrode, with globular bells 43 on either end of the electrode plug, separated by the insulator portion 29. FIG. 5c illustrated a barbell shaped electrode with an additional bell 44 between the bells at either end. FIG. 5d illustrates a multi-flanged electrode assembly, with several flanges 45 extending outwardly from the insulator portion 29. FIGS. 6a through 6c illustrate various forms for the proximal end of the electrode plug, making up the proximal shoulder 38. FIG. 6a illustrates a simple flange 46 on the proximal end of the electrode assembly 24, while FIG. 6b shows a mushroom shaped flange 47, and FIG. 6c illustrates a contoured flange 48. These shapes may be applied to the proximal end (the uteral side of the plug) in order to limit the insertion of the plug into the fallopian tube. FIG. 7 shows a plug having a screw thread 49 outer contour.

Figure 8:
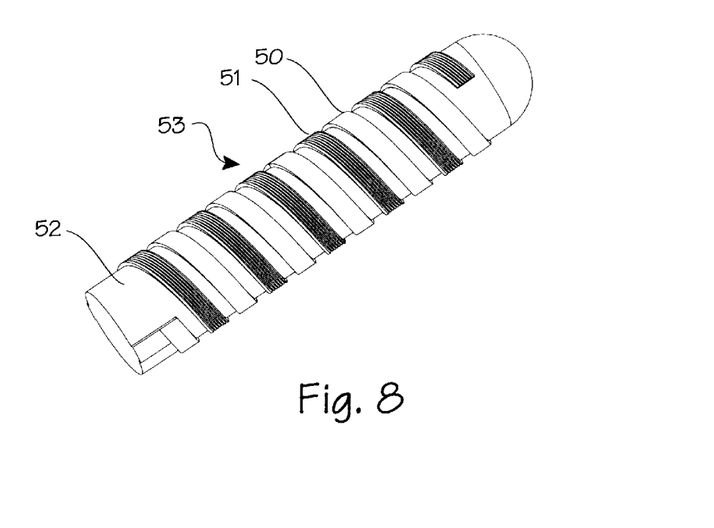
FIG. 8 is a side view of a coil shaped distal electrode.

FIG. 8 illustrates a coil-shape configuration of the distal electrode plug. By manufacturing the electrically conductive material into a wire or strip, it is possible to wind the material over the insulative material to form a coiled electrode. A bipolar coiled plug is made possible by incorporating two separate wires parallel to each other along the coiled length. Thus FIG. 8 includes a helical ground electrode 50 and a helical hot electrode 51 coiled in parallel about insulated plug 52 to form the entire plug assembly 53. The winding pitch or angle between wire and the insulative material being wound on can vary through the plug. By varying the pitch angle, it is possible to create different current density fields for the plug. The pitch can vary from 0° (parallel to the plug's major axis) to 90° (perpendicular to the plug's major axis). In one embodiment, the pitch remains at 0° for the length of the plug and is not wound at all.

Figure 9:
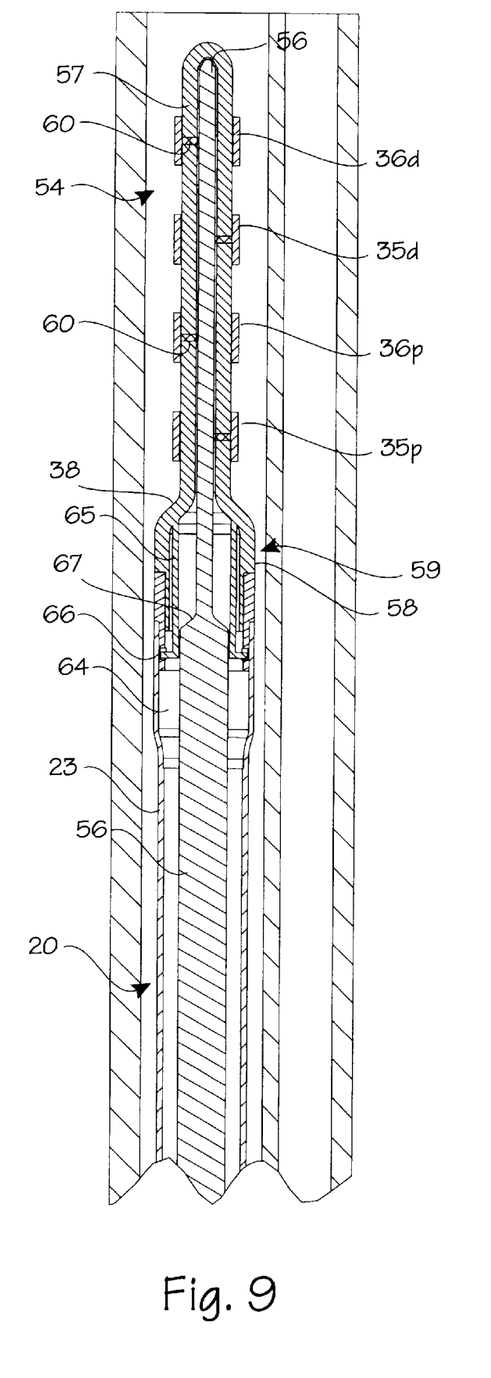
FIG. 9 is a cross section of the delivery catheter.
Figure 10:
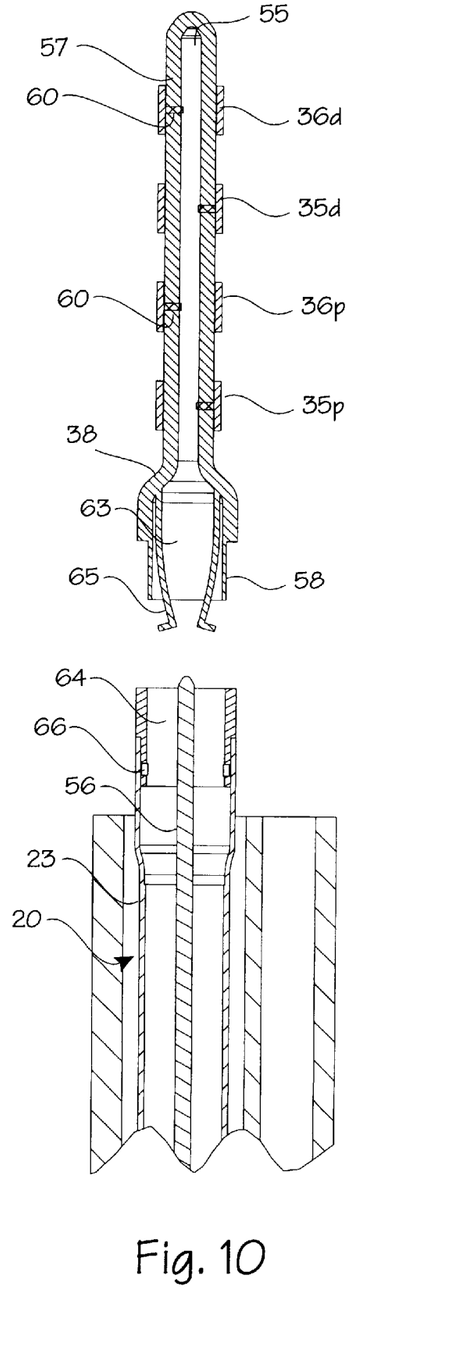
FIG. 10 is a cross section of the electrode plug assembly disconnected from the transcervical catheter.

FIGS. 9 and 10 show cross sections of the delivery catheter with mechanism for delivering energy to the heating tip and disconnecting the tip from the remainder of the catheter. Transcervical catheter 20 is shown housed within the working channel of a hysteroscope 54. The distal tip 23 of the transcervical catheter 20 houses the electrode assembly 24. The electrode plug 24 is a bipolar electrode plug, with a central bore 55 which receives the central conductor assembly 56. The central conductor assembly comprises the necessary wiring to carry energy to the electrode assembly. The electrode assembly includes a electrode plug 57 with a mating assembly 58 at its proximal end 59. The proximal end of the plug is flared, with shoulders 38, designed to ensure that the electrode is not inserted beyond the uterotubal junction. Ground electrodes 36d and 36p and hot electrodes 35d and 35p provide bipolar RF energy to any tissue outside the plug. The electrodes are connected to the remainder of the catheter through electrical contacts 60, and these contacts are further connected to ground wires and hot wires coiled onto the central conductor assembly 56. The mating assembly 58 includes a receiving bore 63 for receiving the central conductor assembly. The distal end of the transcervical catheter likewise has a receiving bore 64 for receiving the spring loaded tangs or detentes 65 which are biased toward the center of the device, but held in radially expanded condition by the thickness of the central conductor assembly 56. The tangs 65 extend into matching receiving holes 66 in the distal end of the insertion catheter 20. The electrical ground wires and hot wires are connected to the RF generator which is outside the body, connected to the proximal end of the transcervical catheter.

In use, as discussed above, the hysteroscope and transcervical catheter are inserted into the uterus through the cervix. Using the hysteroscope, the physician can locate the ostium of the fallopian tube, which corresponds to the uterotubal junction. The physician advances the transcervical catheter out of the hysteroscope, and inserts the plug into the uterotubal junction until the shoulders of the plug are firmly seated in the uterotubal junction. Electrical energy is applied through one or more of the electrodes, grounded through the ground electrodes. When the uterotubal junction has been thermally damaged, it collapses and constricts about the electrode plug. The outer surface of the electrode plug is irregular, allowing mechanical interlock between the uterotubal junction and the plug when the plug constricts over the plug. After heating, the central conductor assembly 56 is pulled proximally while the catheter 20 is held in place. When the central conductor assembly 56 is pulled distally to the point where it clears the tangs, the tangs resiliently rebound to the center of the catheter and fall out of the receiving holes 66, as illustrated in FIG. 10. Should any resistance be encountered, the shoulder 67 on the transition of the central conductor assembly 56 may be used to push gently on the electrode plug while gentle force is applied to the catheter. The deployed plug is left in place to provide permanent occlusion of the fallopian tube. (The process is repeated for each fallopian tube.)

The RF energy may be supplied by any one of numerous RF energy generators available commercially. Although RF energy is currently preferred, microwave energy may also be used, and microwave energy generators suitable for use include such devices as the Prostatron microwave generator currently used for application of microwave energy to the prostate. Microwave power in the frequency of about 100 MHz to 14,000 MHz will also provide sufficient thermal damage to the fallopian tube to initiate collapse and constriction around the electrode.

Figure 11:
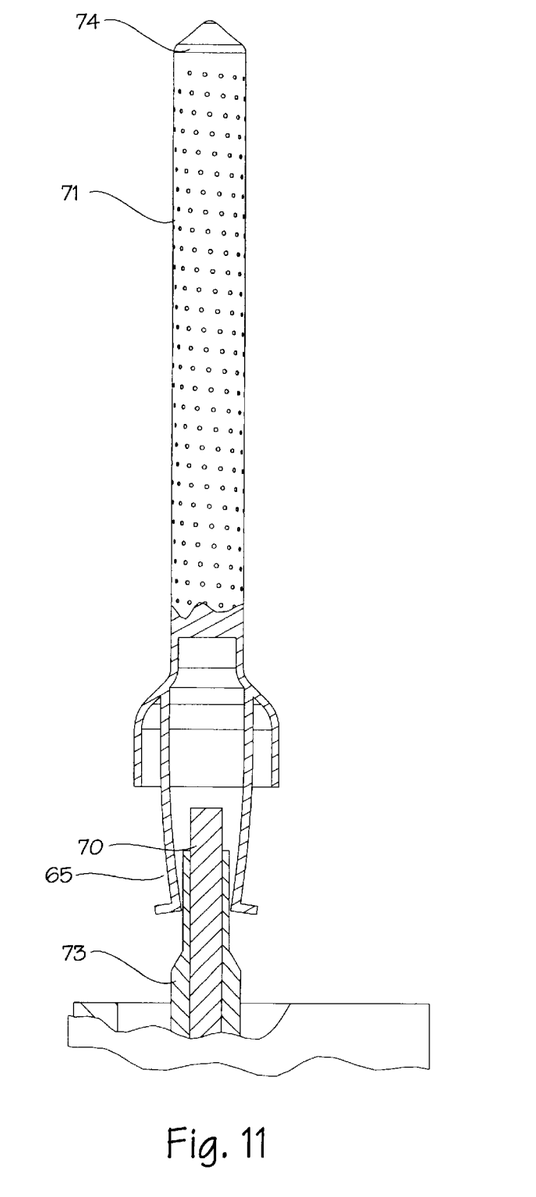
FIG. 11 is a cross section of the occlusion device which uses laser energy and a laser tip to occlude the fallopian tube.

FIG. 11 illustrates an embodiment of the catheter which uses laser light, rather than RF energy, to provide the heat necessary to thermally damage the fallopian tubes and cause them to constrict. In addition to the parts already discussed in relation to the RF embodiment, the laser device shown in FIG. 11 includes a laser light source (not shown), a central conductor 56 comprising fiber optic fiber 70 capable of delivering laser light from the laser source to the tip of the electrode, and a laser heating tip 71 disposed at the distal end of the catheter. The fiber optic fiber is releasably attached to the heating tip with a mechanism such as the releasable detentes described above. (Other mechanisms may include press fitting the fiber optic into a receiving bore in the heating tip so that it may be pulled out of the tip after heating, maintaining the tip in place with force from the catheter outer tube. The optical fiber may also be glued or melted into the tip, and simply snipped with endoscopic cutters after heating.) For this application, laser light sources are commercially available for a variety of other purposes, and these may be readily adapted for use in supplying heating light for the fallopian tubes. The heating tip 71 is a plug of silicone, bioglass or other transparent tip suitable for laser heating, and in this case it is cylindrical. The fiber optic is aimed at the proximal end of a necked down detente holding pin 73, which is inserted into the receiving bore of the heating tip. The distal end of the fiber optic fiber and the distal end of the receiving bore are highly polished to permit maximum transmittance of laser light into the tip. A reflective surface 74 is applied to the distal face of the tip to reflect laser light that reaches the distal face back into the plug. The plug is loaded with dispersive particles (silica, alumina or titania) which serve to disperse the laser energy throughout the plug and convert the energy into heat. When the plug is heated in this manner, it heats the surrounding uterotubal junction tissue to affect the thermal damage which is desirable in the sterilization method. Laser light sources and power ranges typically used for such applications of laser thermal treatment are expected to be safe and sufficient for use in application to the uterotubal junction.

Figure 12:
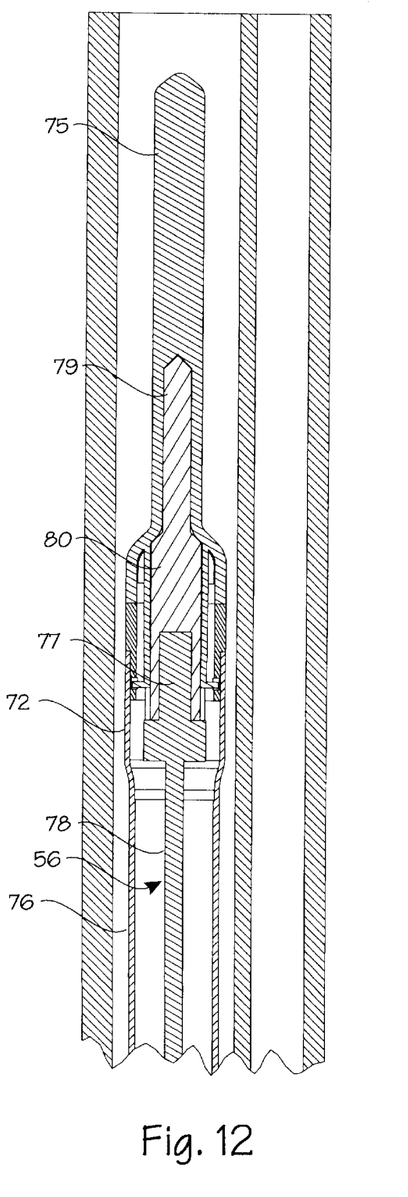
FIG. 12 illustrates an embodiment of the catheter which uses ultrasound energy to occlude the fallopian tube.

FIG. 12 illustrates an embodiment of the catheter which uses ultrasound energy, rather than RF energy, to provide the heat necessary to thermally damage the fallopian tubes and cause them to constrict. FIG. 12 shows the tip of the device, including the plug 75, the transcervical catheter 76, the piezo-electric crystal 77 and electrical conductors 78. The plug is connected to the catheter outer tube 72 of the catheter with a release mechanism similar to that shown in the earlier figures. The coupling element 79 sonically couples the transducer to the plug, and also mechanically couples the transducer to the plug. The coupling element also includes a small diameter distal extension which fits into the bore of the plug during delivery and heating, and permits release of the tangs 65 when the central conductor is pulled proximally and the wide proximal portion 80 clears the tangs. Excitation of the piezoelectric crystal with electrical impulses delivered through the wires will cause the plug 75 and surrounding tissue to heat up, thereby causing the thermal damage to the uterotubal junction desired to cause collapse around the plug. Again, when the uterotubal junction collapses around the plug, the plug can be disconnected from the rest of the transcervical catheter and left in place. Ultrasound energy in the range of 10 KHz to 4 MHz may be applied to effect thermal damage.

Figure 13:
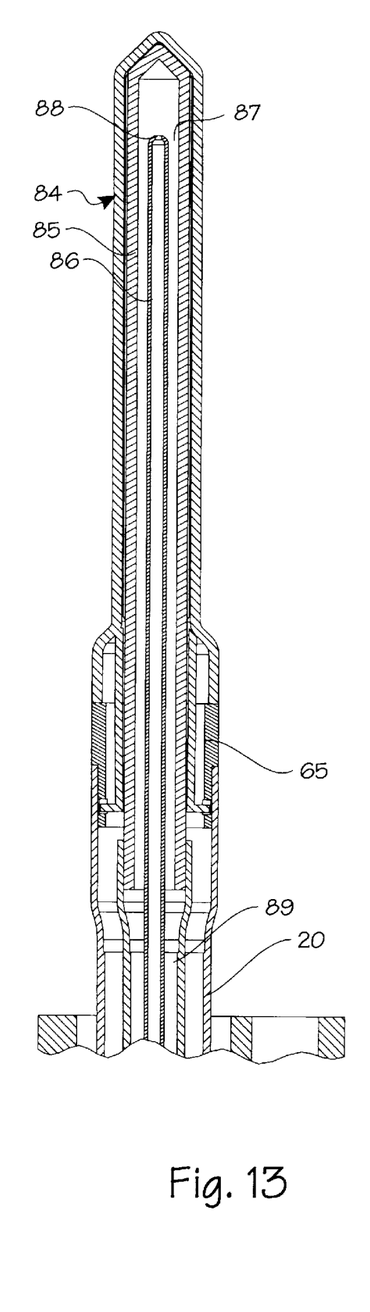
FIG. 13 illustrates an embodiment of the catheter which uses cryogenic energy to occlude the fallopian tube.

FIG. 13 illustrates an embodiment of the catheter which uses cryogenic cooling, rather than heating, to provide the thermal damage necessary to cause the fallopian tubes to constrict. FIG. 13 shows the tip of the device, including the detachable cryogenic plug 84 mounted on the tip of the transcervical catheter 20. The detachable plug in this instance comprises the tip of a cryosurgical probe of the type that uses liquid nitrogen. Cooling of the plug is accomplished by cryogenic cooling of the jacket 85 which fits closely within the plug. The cryogenic supply line 86 communicates with the annular lumen 87 formed between the jacket 85 and the supply line. The supply line includes a port 88 at the distal tip, to distribute cryogenic fluid into the jacket. Liquid nitrogen or other cryogenic is supplied to the probe through the supply line, and exhausts out the annular lumen and the gas return line 89. After application of cryogenic cooling, the gas line is pulled proximally until the jacket clears the tangs 65 of the release mechanism, at which point the tangs release the catheter 20 and the plug is left in place.

Another embodiment of the device is one which accomplishes conductive and convective heating through the plug to accomplish the same results. There are several other ways to heat the fallopian tube through the plug by conductive and convective techniques. For example, AC or DC current can be delivered directly through the plug to create resistive heating of the plug which in turn generates a hot surface on the plug. Another possible technique is the delivery of a hot gas or hot liquid through channels of the catheter to the plug.

A plug could be designed with a resistive element placed with the plug to heat the plug and its surface. Heat would be transferred to the uterotubal junction by conduction and/or convection. Conduction of heat from the plug surface to the uterotubal junction is accomplished by placing the plug in direct contact with the uterotubal junction. Convection of heat from the plug surface to the uterotubal junction is accomplished by transfer of heat from the plug surface to fluids in the area of the plug such as body fluids or artificial liquids, and this fluid in turn transfers heat to the uterotubal junction.

Figure 14:
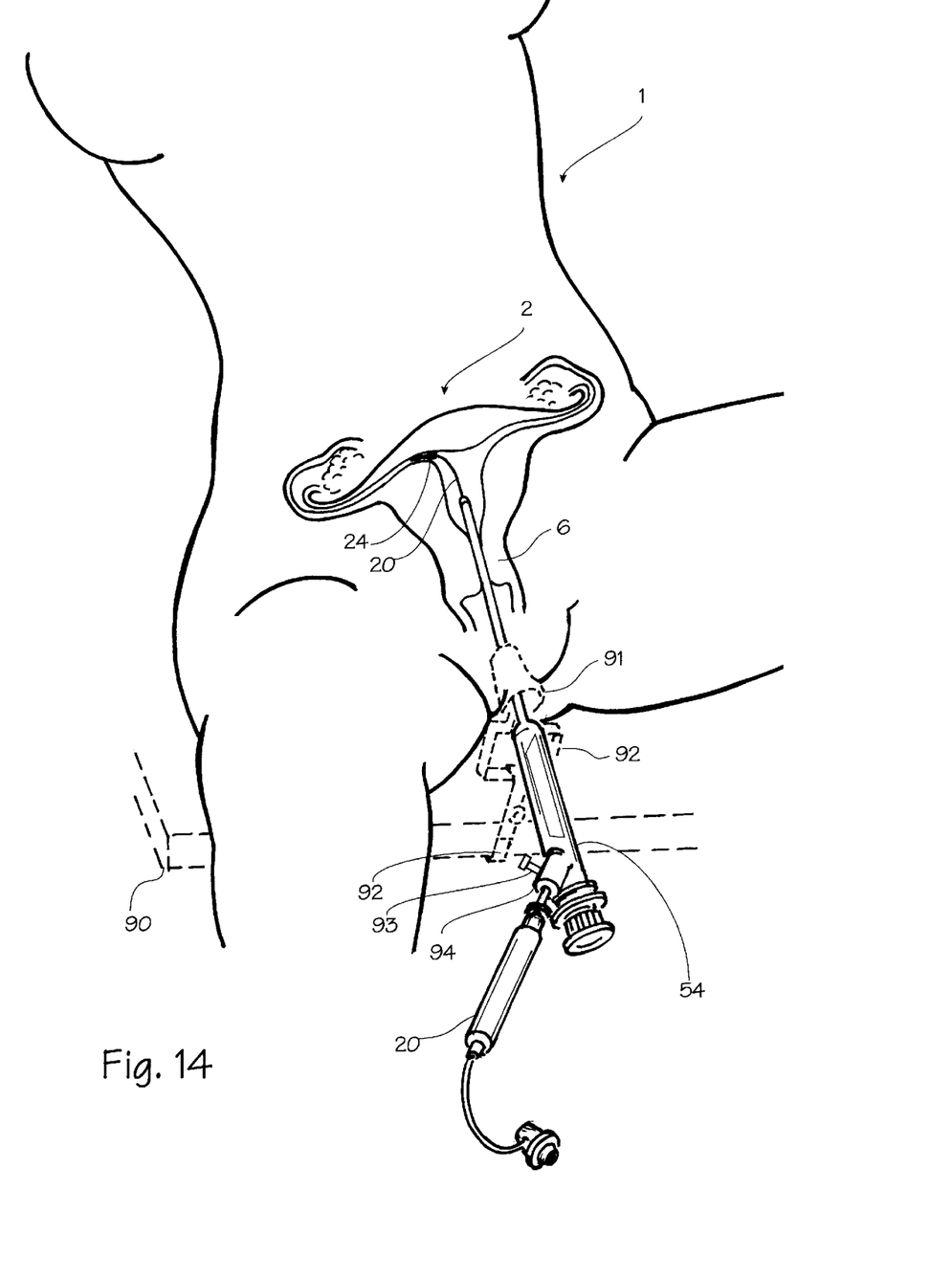
FIG. 14 is an overview of the female body illustrating major aspects of the sterilization method.

FIG. 14 illustrates the overall method of using the devices described in this patent. The patient 1 lays on an operating table 90, in position similar to that used for a gynecology exam, providing access to the vagina 8. Access to the cervix 6 and uterus 2 is facilitated by insertion and opening of the speculum 91, which is locked to the operating table 90 with clamping mechanism 92. The physician inserts the hysteroscope 54 to find and inspect the opening into the fallopian tubes (called the ostium), and then inserts the transcervical catheter 20 and advances the transcervical catheter until the plug is seated in the ostium of the fallopian tube. When the plug is properly positioned, the physician will then use the catheter locking mechanism 93 (the illustrated locking mechanism is a set screw installed on the hysteroscope access port 94) to fix the transcervical catheter in place and prevent accidental removal of the plug during the procedure or during release of the plug. The speculum clamp and catheter locking mechanism form a locking jig which includes one clamp for fixing the scope to the operating table and a second clamp for securely holding the proximal end of the transcervical catheter. (With the transcervical catheter locked in place in this manner, the physician may safely apply energy to the releasable tip without fear of inadvertently pulling the plug uterotubal junction and misapplying the required energy.) The physician then applies energy sufficient to cause the uterotubal junction to collapse about the catheter tip. After collapse and constriction has been confirmed (this may be done visually through the hysteroscope, or by comparison of electrode impedance in the RF embodiments), the physician will hold the outer body of the transcervical catheter firmly and pull the central conductor from the plug. (Again, with the transcervical catheter locked in place, the physician may safely withdraw the central conductor from the plug without fear of inadvertently pulling the plug from the thermally damaged uterotubal junction.) With the central conductor removed from the plug, the catheter should fall away from the plug. The physician will then remove the catheter. For complete sterilization, the physician will then repeat the procedure on the other side of the uterus. (Various embodiments of locking mechanisms may be used, and will suffice to immobilize the catheter in relation to the patient by any locking means. Where a hysteroscope is not used, or is provided without the locking screw as illustrated, it will suffice to lock the catheter to the speculum. It will also be sufficient to lock the speculum to the hysteroscope and use the friction between the working channel of the scope and the catheter to stabilize the catheter and avoid excessive movement of the purse. The number of possible locking mechanism embodiments is vast.)

Immediately after delivery of the RF energy to the targeted tissue, several stages of tissue response will occur in the healthy female. First, the damaged tissue will undergo an acute inflammatory response. In this stage, serum and white blood cells exit from the blood vessels near the tissue and move into the interstitial space between the cells. This process is called edema. This process is accompanied by the release of products from the mast cells, which increase the vascular permeability to serum and white blood cells, increasing the edema. Giant cells called macrophages then move into the damaged tissue and start digesting the thermally damaged cells.

The next stage of response is the healing stage, in which repair mechanisms take place to restore the uterotubal junction to its original condition. In this stage, cytokines and other products released by the mast cells stimulate the fibroblasts of the conjunctive tissue (under the endosalpinx) which duplicate and migrate into the area of the destroyed tissue. The fibroblasts then produce a matrix of gel like material and fibers in which the fibroblasts proliferate. This process is called colonization, and continues until the entire damaged area is filled with fibroblasts. The blood vessels in the injured area form buds which grow into the new fibroblast matrix and revascularize the newly formed tissue.

The plug which is left behind in the uterotubal junction will be maintained in place by the constrictive action of the damaged tissue, during the healing process. As an aid to long term retention, the plug is porous to a degree which allows endothelial tissue and/or conjunctive tissue of the uterotubal junction to grow into the pores of the plug. The presence of the artificial matrix such as the plug provides an opportunity for the fibroblasts to grow into the plug and favors occlusion of the fallopian tube in the area of the plug. To enhance tissue adhesion to the plug, each of the plugs illustrated above may be made of a porous material (metal, glass, ceramic or other material) with pores ranging from about 1–400 microns. The pores may be natural to the material, or they may be manufactured into the material. (For example, metal plugs with pores may be manufactured as reticulated or foamed metals according to known techniques.)

Tissue in-growth can be promoted by application of in-growth promoting compounds such P15 or HEP III to the porous plug. Such agents that promote either the attachment of cells to the plug or the cellular growth deep into the pores and surface features (nooks and crannies) of the plug. Examples of such agents include protein coatings such as collagen, fibronectin, and transforming growth factor beta, or a synthetic polypeptide coatings such as P15 (Gly-Thr-Pro-Gly-Pro-Gln-GLy-Ile-Ala-Gly-Gln-Arg-Gly-Val-Val) or HEP III (GLy-Glu-Phe-Tyr-Phe-Asp-Leu-Arg-Leu-Lys-Gly-Asp-Lys), The manufacture of these compounds is well described in Bhatnagar, *Synthetic Compounds And Compositions With Enhanced Cell Binding*, U.S. Pat. No. 5,635,482 (Jun. 3, 1997) and Tsilibary, *Prosthetic Devices Coated With A Polypeptide With A Type IV Collagen Activity*, U.S. Pat. No. 5,152,784 (Oct. 6, 1992). Coating of the device by these proteins or polypeptides can be accomplished by dipping the plug into a solution or liquid suspension of the coating. This may be done immediately before implanting the plugs into the uterotubal junction, merely by dipping or glomming P15 suspension onto the plug. The coating may also be applied during manufacture using dipping and coating techniques commercially available from such companies as Peptide Innovations, Inc. of Southfield, Mich. Additionally, the in-growth promoting compound may be injected to the vicinity of the plug after the plug has been implanted or before implantation. Although heat will be generated in the vicinity of the plug, the in-growth promoting compound is not damaged.

The P15 compound appears to permit direct attachment of new endothelial cells to the plug material, and the endothelial cells are further attached to the uterotubal junction, thus securing the plug in place. The compound also appears to encourage endothelial growth sufficient to create a matrix of endothelial cells which is mechanically intermingled with the porous structure of the plug.

The power requirements and length of time that energy must be applied to the uterotubal junction are modest, on the order of a few watts of power for several seconds. In initial experiments, a range of power and application time proved useful in constricting body tissue. In one experiment, we tested the effects of RF energy on bovine coronary arteries. A catheter was placed within the arterial structure and 10 watts of RF energy were delivered to the distal electrode for about 10 seconds. The artery constricted tightly on the catheter tip electrode. The diameter of the artery was measured at 0.064 inches with about 3 cm of the artery cut out of the myocardium. The experiment was repeated and the catheter was slowly dragged through the artery while the RF energy was delivered. The artery and its surrounding tissue were cut in half for observation. The RF energy delivered through the electrode constricted and closed the artery.

In a second experiment, we tested the effect of RF energy applied through a catheter on a uterus and fallopian tubes of a large sow (500 lbs.). We separated the uterotubal junction, fallopian tubes and ovaries from the reproductive system. We then placed a 7F steerable electrophysiology catheter with a 4 mm long tip through the uteral end into the fallopian tube. We applied 5 watts of power for 15 seconds. This caused necrosis, tissue discoloration and occlusion at the electrode position. A small amount of force was required to remove the electrode.

In a third test, we tested the seal provided by a removable electrode after RF treatment. We inserted a dumbbell-shaped electrode into the uterotubal junction of a large sow, and applied ten watts of energy for 20 seconds. This caused necrosis, tissue discoloration and occlusion at the electrode position. A tensile tester was then attached to the electrode wire and pulled up to a force of 0.5 pounds without dislodging the electrode. With the electrode left in place, we placed a syringe needle into the distal section of the fallopian tubes and tied off the fallopian tubes around the needle with suture. We then attached an ACS PTCA indeflator containing diluted blue dye to the needle and applied pressure at about 20 psi for 15 minutes. We then attached a syringe of pure dye to the needle and applied a relatively high amount of pressure for 2 minutes. Blue dye was observed dripping out of the distal section of the fallopian tubes, through the tied off segment around the needle. None of the dye leaked past the plug into the uterus.

Variations in the devices presented above are expected to arise in practice of the inventions. For example, the optimal power settings and time for application of energy will most likely be refined with broader experience with the devices. It is expected that additional material for the plug will be developed and employed in the practice of the inventions. It is also expected that new in-growth promoting compounds will be discovered and applied in the practice of inventions. The plug may also be designed to be removed at a later date, either by removing a central core or by collapsing in on its self.

Finally, although the inventive methods and devices have been described in the environment of human sterilization, they may be applied in numerous animals for which sterilization is often desired. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method for sterilizing a female patient using an elongated instrument assembly having a distal end, said method comprising the steps of:

inserting the distal end of the elongated instrument assembly into the uterine tube of the female patient, the distal end of the elongated instrument having a detachable plug;

applying tissue damaging means from the plug to the uterine tube thereby causing the tissue of the uterine tube to collapse on the plug;

detaching the plug from the distal end of the elongated instrument assembly; and removing the remaining portion of the elongated instrument assembly from the female patient.

2. The method of claim 1 wherein the tissue damaging means is selected from the group consisting of radio frequency energy, laser light, electrical energy, cryogenic cooling and ultrasonic waves.

3. A method for sterilizing a female patient using an elongated instrument assembly having a distal end, the female patient being supported, during the procedure, on an operating table and access to the uterus is facilitated by installation of a speculum in the vagina of the female patient, said method comprising the steps of:

clamping the speculum to the operating table;

inserting the distal end of the elongated instrument assembly into the uterine tube of the female patient, the distal end of the elongated instrument having a detachable plug;

locking the elogated instrument assembly to the speculum;

applying tissue damaging means from the plug to the uterine tube thereby causing the tissue of the uterine tube to collapse on the plug;

detaching the plug from the distal end of the elongated instrument assembly; and removing the remaining portion of the elongated instrument assembly from the female patient.

4. The method of claim 3 wherein the tissue damaging means is selected from the group consisting of radio frequency energy, laser light, electrical energy, cryogenic cooling and ultrasonic waves.

* * * * *